(12) United States Patent
Baird

(10) Patent No.: US 6,298,855 B1
(45) Date of Patent: *Oct. 9, 2001

(54) SURGICAL DRAPE

(75) Inventor: Daniel Duncan Baird, Woodstock, GA (US)

(73) Assignee: Kimberly-Clark Worldwide, Inc., Neenah, WI (US)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/426,922

(22) Filed: Oct. 22, 1999

(51) Int. Cl.[7] ................................................. A61B 19/00
(52) U.S. Cl. .................................... 128/849; 128/853
(58) Field of Search ................................. 128/849–856

(56) References Cited

U.S. PATENT DOCUMENTS

| | | | |
|---|---|---|---|
| D. 333,404 | 2/1993 | Thompson | D6/602 |
| 3,503,391 | 3/1970 | Melges | 128/132 |
| 3,667,458 | 6/1972 | Krebs | 128/132 |
| 3,668,050 | 6/1972 | Donnelly | 161/39 |
| 3,669,106 | 6/1972 | Schrading et al. | 128/132 D |
| 3,763,857 | 10/1973 | Schrading | 128/132 D |
| 3,791,381 | 2/1974 | Krzewinski | 128/132 D |
| 3,799,161 | 3/1974 | Collins | 128/132 D |
| 3,856,006 | 12/1974 | Krzewinski | 128/132 D |
| 3,882,859 | 5/1975 | Ericson | 128/132 D |
| 3,892,617 | 7/1975 | DePriest et al. | 156/353 |
| 3,902,484 | 9/1975 | Winters | 128/132 D |
| 3,910,268 | 10/1975 | Miller | 128/132 D |
| 3,930,497 | 1/1976 | Krebs et al. | 128/132 D |
| 4,024,862 | 5/1977 | Collins | 128/132 D |
| 4,027,665 | 6/1977 | Scrivens | 128/132 |
| 4,041,942 | * 8/1977 | Dougan | 128/853 |
| 4,059,104 | 11/1977 | DePriest et al. | 128/132 D |
| 4,089,331 | 5/1978 | Hartigan et al. | 128/132 D |
| 4,196,723 | 4/1980 | Moose, Jr. | 128/132 D |
| 4,275,720 | 6/1981 | Wichman | 128/132 D |
| 4,323,062 | 4/1982 | Canty | 128/132 D |
| 4,336,797 | 6/1982 | Lutacca et al. | 128/132 D |
| 4,378,794 | 4/1983 | Collins | 128/132 D |
| 4,466,430 | 8/1984 | Shultz | 128/132 D |
| 4,476,860 | 10/1984 | Collins et al. | 128/132 D |
| 4,890,628 | 1/1990 | Jackson | 128/849 |
| 5,010,899 | 4/1991 | Thompson | 128/849 |
| 5,109,873 | 5/1992 | Marshall | 128/849 |
| 5,197,493 | 3/1993 | Grier-Idris | 128/853 |

(List continued on next page.)

FOREIGN PATENT DOCUMENTS

| | | |
|---|---|---|
| 0 297 065 | 12/1988 | (EP) . |
| 432 728 A1 | 6/1991 | (EP) . |
| 436 852 A1 | 7/1991 | (EP) . |
| 724 412 B1 | 5/1999 | (EP) . |
| 95/10986 | 4/1995 | (WO) . |
| 99/33408 | 7/1999 | (WO) . |
| 99/37234 | 7/1999 | (WO) . |

OTHER PUBLICATIONS

Kimberly–Clark's 1999–2000 Product Catalog, pp. 79–80.

*Primary Examiner*—Michael A. Brown
(74) *Attorney, Agent, or Firm*—Scott B. Garrison

(57) ABSTRACT

The present invention is directed toward a surgical drape having a base sheet including a primary fenestration and at least one secondary fenestration, the drape being suitable for use in surgical procedures having multiple surgical sites.

20 Claims, 13 Drawing Sheets

U.S. PATENT DOCUMENTS

| | | | |
|---|---|---|---|
| 5,222,507 | 6/1993 | Taylor | 128/849 |
| 5,322,071 | 6/1994 | Ambrose | 128/849 |
| 5,339,831 * | 8/1994 | Thompson | 128/852 |
| 5,341,821 | 8/1994 | DeHart | 128/849 |
| 5,394,891 | 3/1995 | Mills et al. | 128/852 |
| 5,398,700 | 3/1995 | Mills et al. | 128/853 |
| 5,454,381 | 10/1995 | DeHart | 128/849 |
| 5,464,024 | 11/1995 | Mills et al. | 128/849 |
| 5,471,999 * | 12/1995 | Mills | 128/853 |
| 5,515,868 | 5/1996 | Mills | 128/854 |
| 5,538,012 | 7/1996 | Wiedner et al. | 128/853 |
| 5,611,356 | 3/1997 | Rothrum | 128/849 |
| 5,765,566 | 6/1998 | Rothrum | 128/849 |
| 5,778,891 | 7/1998 | McMahan | 128/849 |
| 5,803,086 | 9/1998 | Scholz et al. | 128/849 |
| 5,832,927 | 11/1998 | Wijesinghe et al. | 128/849 |
| 5,860,420 | 1/1999 | Wiedner et al. | 128/853 |
| 5,875,780 | 3/1999 | Rodriguez | 128/849 |
| 5,901,706 | 5/1999 | Griesbach et al. | 128/849 |
| 5,988,172 * | 11/1999 | Sosebee | 128/852 |

* cited by examiner

SURGICAL DRAPE

FIELD OF THE INVENTION

The present invention relates generally to surgical drapes, and more particularly to surgical drapes suitable for spinal intervention procedures.

BACKGROUND OF THE INVENTION

Drapes are used during surgical procedures to create and maintain a sterile environment about the surgical site. Draping materials are selected to create and maintain an effective barrier that minimizes the passage of microorganisms between non-sterile and sterile areas. To be effective, a barrier material should be resistant to blood, aqueous fluid, and abrasion, as lint-free as possible, and drapable. When used during surgery, drapes prevent blood and other bodily fluids from contaminating the sterile field.

A variety of surgical drapes exist, but most share several common features. Most drapes are made of a water-repellent or water-impermeable material, or are coated with such a material, to prevent the passage of bodily fluids as well as contaminating microorganisms. Many of today's surgical drapes are made of disposable nonwoven fabrics, plastic film, or papers.

Surgical drapes will commonly have an opening or aperture (more commonly known in the medical field as a "fenestration") through which the surgical procedure is performed. In certain procedures, more than one surgical site is used. In these more complex procedures, the patient must be draped using a plurality of drapes or must be re-draped between procedures.

An adhesive material may be attached to the periphery of the drape material about the fenestration so that the drape can be held in place around the surgical site and so that blood will not pass between the drape and the patient's body. The combination of the drape itself and the adhesive material around the perimeter of the aperture ensures a barrier between the surgical wound and the remainder of the body. Some drapes utilize incise materials which extend over the fenestration. The incise materials are typically transparent plastic films having an adhesive side which adheres to the surgical site of the patient. In such draping systems, the drape is secured to the patient by at least the incise material.

Electric cords and suction lines running along the patient are usually clamped or tied to the edges of the outer sheet on the surgical table. These cords or lines can become entangled, and when pulled may cause devices to fall to the floor and become unsterile. The clamps and ties are usually not versatile or strong enough to allow easy addition or removal of tubes and electrical lines. This results in delay in surgery while operating room personnel undo and re-affix clamps. Providing drapes that are suitable for use in surgical procedures adequate mechanisms to secure such cords and lines remains a concern of health care professionals.

To minimize the costs and risks associated with surgical procedures, it is desirable to provide a one-piece drape that is easy to apply, provides multiple surgical sites and adequate mechanisms for retention of cords and lines, and may be tailored for specific types of surgery.

SUMMARY OF THE INVENTION

In response to the foregoing problems and difficulties encountered by those of skill in the art, the present invention is directed toward a surgical drape for covering a patient during a surgical procedure. The drape includes a base sheet having an upper surface, a lower surface, a forward edge, and a rearward edge. The drape of the present invention further includes a primary fenestration that is formed in the base sheet through which a surgical procedure may be performed when the drape is covering a patient. In some embodiments, at least one secondary fenestration formed in the base sheet through which a second surgical procedure may be performed when the drape is covering a patient. In certain embodiments, two secondary fenestrations may be utilized.

A reinforcement panel may be disposed about the primary fenestration, and in some embodiments, about the secondary fenestrations. The reinforcement panel may be positioned on the upper surface of the base sheet and includes reinforcement fenestrations that are aligned with the primary fenestration and, if necessary, the secondary fenestrations.

An incise layer may also be provided, the incise layer being disposed over the primary and secondary fenestrations and disposed between the reinforcement panel and the base sheet. The incise layer includes an adhesive side that is adapted to adhere to the patient when the drape is covering the patient. In some procedures, particularly those procedures which take a long time, it is important that the incise layer be "breathable" by exhibiting high moisture vapor transmission rates. Thus, the adhesive side of the incise layer faces downwardly when the drape is positioned over the patient. Release layers may be provided on the adhesive side of the incise layer to permit easy handling and maintain sterility of the incise layer.

The drape of the present invention may be further adapted to be positionable over the patient so that the primary fenestration is disposed proximate to the spine of the patient, and the secondary fenestration is disposed proximate to the bone graft site of the patient. At least one pouch may further be provided, the pouch being releasably attachable to the upper surface of the drape.

The surgical drape of the present invention may be folded so that, as medical personnel apply the drape to the patient, the lower surface of the drape is on the exterior of the folded drape, and the release layer covering the primary fenestration is clearly visible and easily accessible by the medical personnel. In some embodiments, the release layer disposed over the incise layer of the primary fenestration is segmented so that a portion of the adhesive side of the incise layer may be exposed and applied to the patient. In such an embodiment, additional portions of the incise layer of the fenestration may be exposed and applied to the patient, if necessary.

Additionally, pouches may be provided which have an upper edge which are attached to the surgical drape, and a lower portion that is releasably adhered to the drape. Such a configuration permits electrical cords, suction lines and the like to be routed beneath the pouch and held securely in place.

Other objects, advantages and applications of the present invention will be made clear by the following detailed description of a preferred embodiment of the invention and the accompanying drawings wherein reference numerals refer to like or equivalent structures.

DETAILED DESCRIPTION OF THE PRESENT INVENTION

Figure 1:
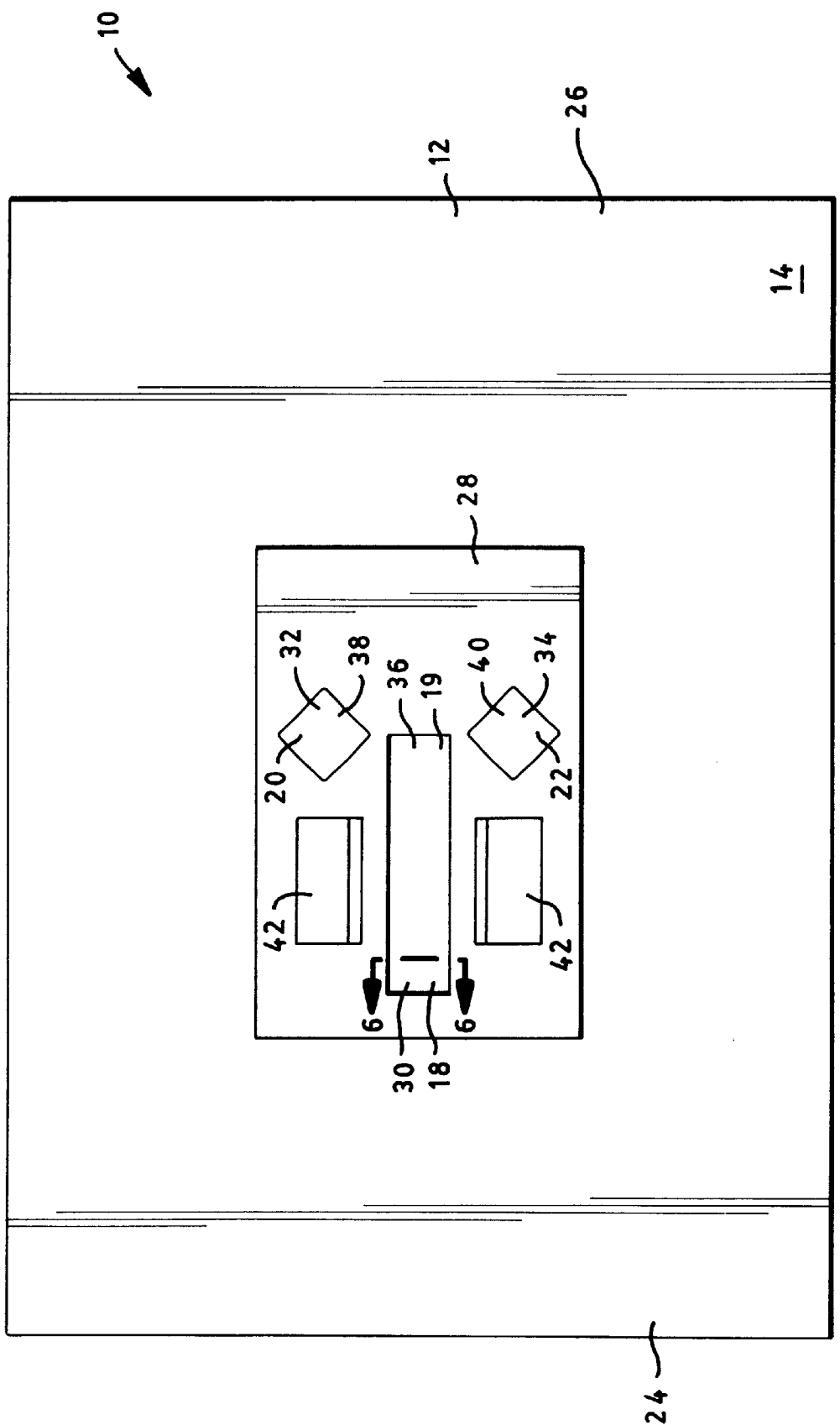
FIG. 1 is a top view of an embodiment of the drape according to the present invention.

In response to the foregoing challenges that have been experienced by those of skill in the art, the present invention is directed toward a drape suitable for use in surgical procedures performed on the spine. The surgical drape 10 of the present invention is illustrated in FIG. 1 and includes a base sheet 12 having an upper surface 14 and a lower or patient-contacting surface 16, best shown in FIG. 2. Although it may have varying dimensions and shapes, drape 10 is normally rectangular and sized to cover at least a majority of a patient's body during a surgical procedure. The width A and the length B of the drape may vary. In selected embodiments, the width A may be within the ranges of 70 to 100 inches (178 to 254 cm), or 80 to 90 inches (203 to 229 cm), or 85 to 90 inches (216 to 229 cm). In some embodiments, the width A of the drape may be 88 inches (224 cm). The length B of the drape may also vary, but may be within the ranges of 100 to 160 inches (245 to 406 cm), or 110 to 140 inches (279 to 356 cm), or 120 to 130 inches (305 to 330 cm). In selected embodiments, the length B of the drape 10 may be 124 inches (315 cm). As used herein, any given range is intended to include any and all lesser included ranges. For example, a range of from 45–90 would also include the ranges of from 50–90, 45–30, 46–89, etc.

The base sheet 12 may be made from a wide variety of materials, including, for example, woven, reusable fabrics and nonwoven disposable fabrics or webs. Nonwoven materials suitable for use with the present invention include, for example, multilayer laminates such as a spunbonded/ meltblown/spunbonded ("SMS") material. An example of a suitable fabric is disclosed in U.S. Pat. No. 4,041,203, which is hereby incorporated by reference.

As used herein the term "nonwoven fabric or web" means a web having a structure of individual fibers or threads that are interlaid, but not in an identifiable manner as in a knitted fabric. Nonwoven fabrics or webs have been formed from many processes such as for example, meltblowing processes, spunbonding processes, and bonded carded web processes. The basis weight of nonwoven fabrics is usually expressed in ounces of material per square yard (osy) or grams per square meter (gsm) and the fiber diameters useful are usually expressed in microns. (Note that to convert from osy to gsm, multiply osy by 33.91).

As used herein the term "spunbonded fibers" refers to small diameter fibers which are formed by extruding molten thermoplastic material as filaments from a plurality of fine, usually circular capillaries of a spinneret with the diameter of the extruded filaments then being rapidly reduced as by, for example, in U.S. Pat. No. 4,340,563 to Appel et al., and U.S. Pat. No. 3,692,618 to Dorschner et al., U.S. Pat. No. 3,802,817 to Matsuki et al., U.S. Pat. Nos. 3,338,992 and 3,341,394 to Kinney, U.S. Pat. No. 3,502,763 to Hartman, and U.S. Pat. No. 3,542,615 to Dobo et al. Spunbond fibers are generally not tacky when they are deposited onto a collecting surface. Spunbond fibers are generally continuous and have average diameters (from a sample of at least 10) larger than 7 microns, more particularly, between about 10 and 20 microns.

As used herein the term "meltblown fibers" means fibers formed by extruding a molten thermoplastic material through a plurality of fine, usually circular, die capillaries as molten threads or filaments into converging high velocity, usually hot, gas (e.g. air) streams which attenuate the filaments of molten thermoplastic material to reduce their diameter, which may be to microfiber diameter. Thereafter, the meltblown fibers are carried by the high velocity gas stream and are deposited on a collecting surface to form a web of randomly disbursed meltblown fibers. Such a process is disclosed, for example, in U.S. Pat. No. 3,849,241 to Butin et al. Meltblown fibers are microfibers that may be continuous or discontinuous, are generally smaller than 10 microns in average diameter, and are generally tacky when deposited onto a collecting surface.

As used herein "multilayer laminate" means a laminate wherein some of the layers are spunbond and some meltblown such as a spunbond/meltblown/spunbond (SMS) laminate and others as disclosed in U.S. Pat. No. 4,041,203 to Brock et al., U.S. Pat. No. 5,169,706 to Collier, et al, U.S. Pat. No. 5,145,727 to Potts et al., U.S. Pat. No. 5,178,931 to Perkins et al. and U.S. Pat. No. 5,188,885 to Timmons et al. Such a laminate may be made by sequentially depositing onto a moving forming belt first a spunbond fabric layer, then a meltblown fabric layer and last another spunbond layer and then bonding the laminate in a manner described below. Alternatively, the fabric layers may be made individually, collected in rolls, and combined in a separate bonding step. Such fabrics usually have a basis weight of from about 0.1 to 12 osy (6 to 400 gsm), or more particularly from about 0.75 to about 3 osy. Multilayer laminates may also have various numbers of meltblown layers or multiple spunbond layers in many different configurations and may include other materials like films or coform materials, e.g. SMMS, SM, SFS, etc.

As used herein, the term "coform" means a process in which at least one meltblown diehead is arranged near a chute through which other materials are added to the web while it is forming. Such other materials may be pulp, superabsorbent particles, cellulose or staple fibers, for example. Coform processes are shown in commonly assigned U.S. Pat. No. 4,818,464 to Lau and U.S. Pat. No. 4,100,324 to Anderson et al. Webs produced by the coform process are generally referred to as coform materials.

Figure 3:
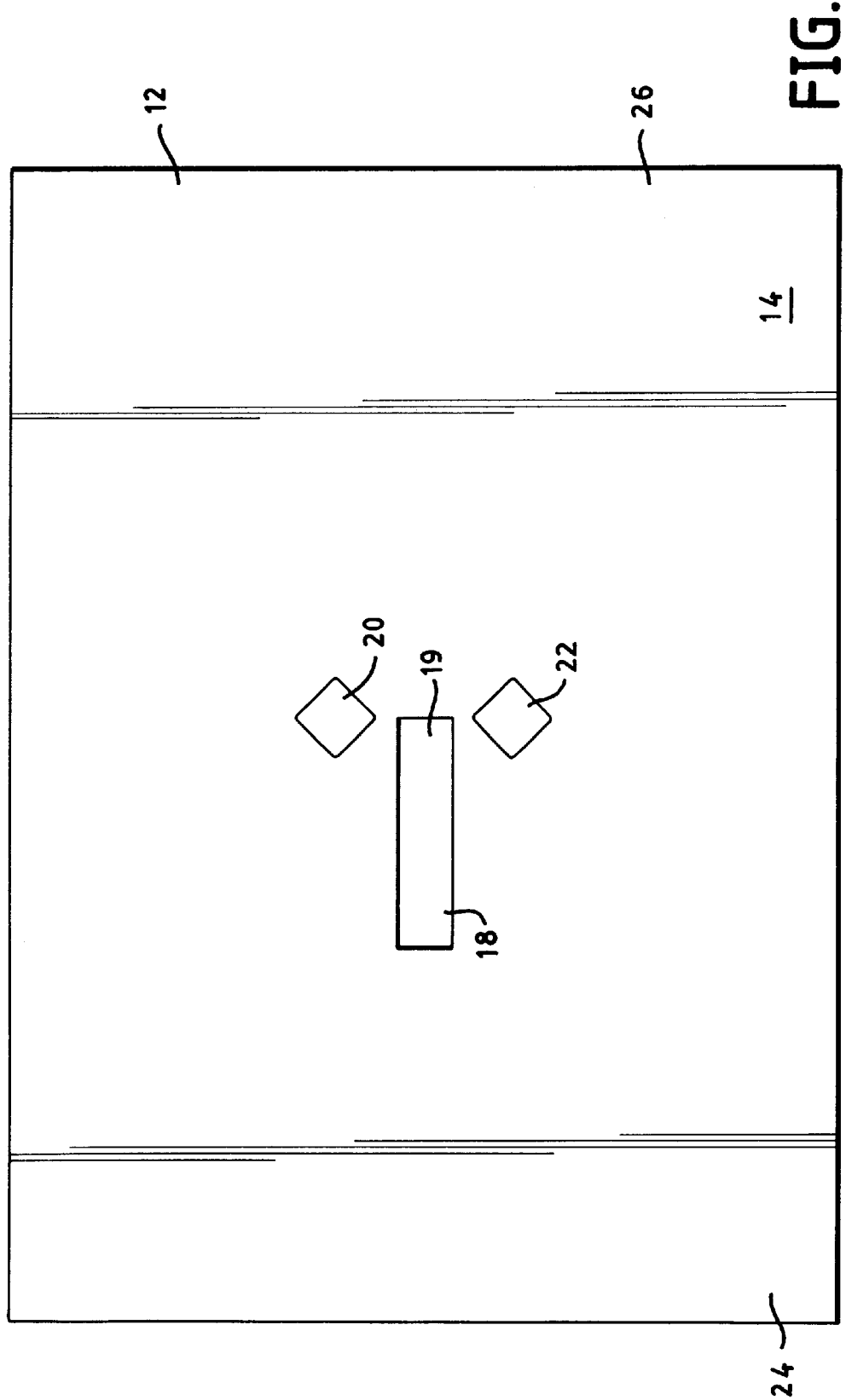
FIG. 3 is a top view of an embodiment of a base sheet according to the present invention.

Referring now to FIG. 3, the base sheet 12 is shown therein and includes a primary fenestration 18 and at least one secondary fenestration 20. As shown therein, two secondary fenestrations 20 and 22 are provided. The primary fenestration 18 is rectangular in shape, while the secondary fenestrations 20 and 22 are square. However, it is contemplated that any of the fenestrations utilized in the present invention may have various other shapes.

Figure 8:
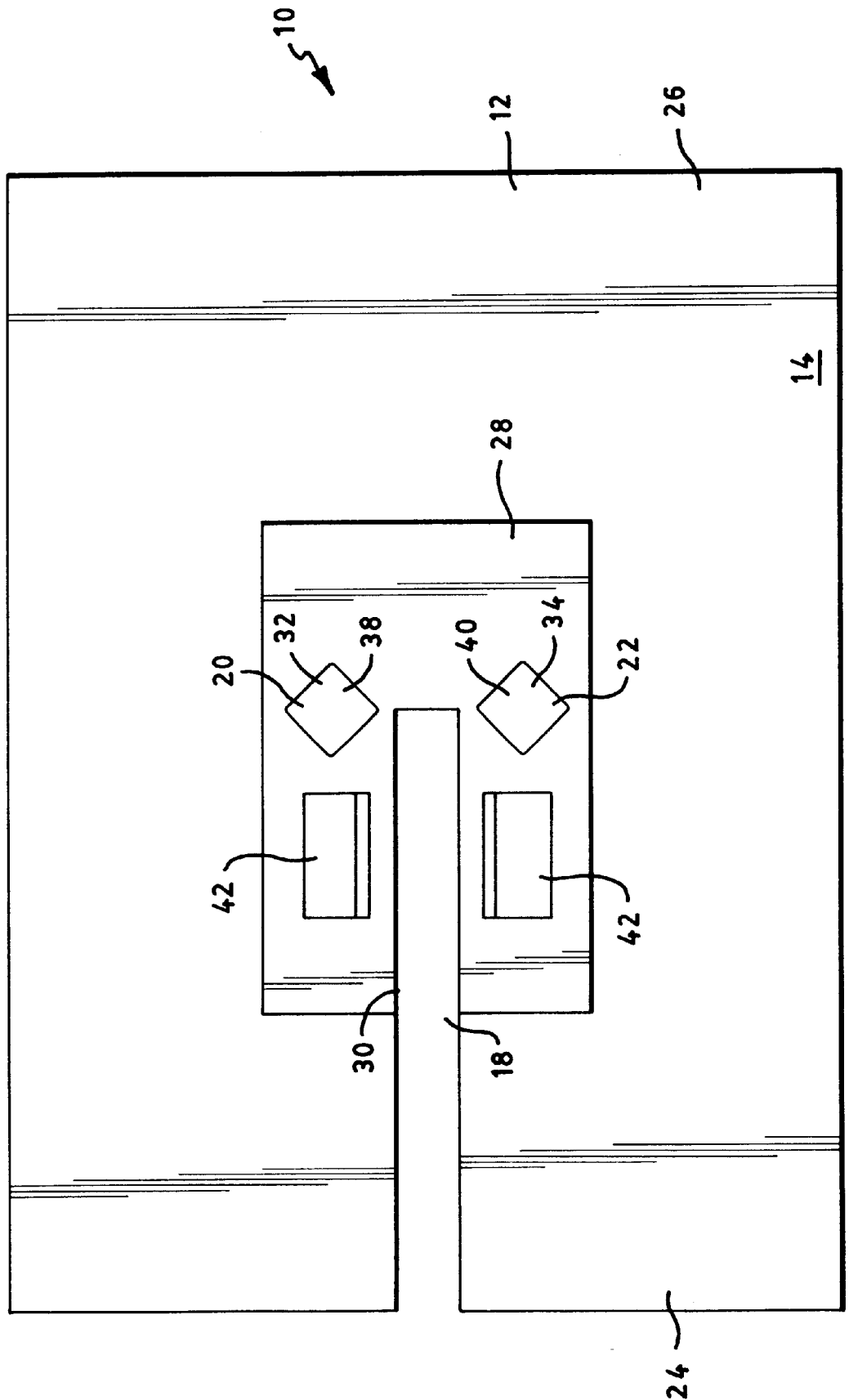
FIG. 8 is a top view of another embodiment of the drape according to the present invention.

The drape 10 depicted in FIG. 8 illustrates an additional configuration of the primary fenestration 18. As shown therein, the fenestration 18 is formed as a slot extending up to the forward edge 24 of the base sheet 12. In such an embodiment, an incise layer may not be provided for the primary fenestration 18. The drape shown in FIG. 9 includes a primary fenestration 18 that is square.

The primary fenestration 18 is positioned within the base sheet 12 so that, when the drape 10 is applied to the patient, the primary fenestration 18 is disposed over the surgical site for the spinal surgery. For example, if the patient is lying face down on the surgical table, the primary fenestration 18 is disposed over at least a portion of the patient's spine.

Figure 2:
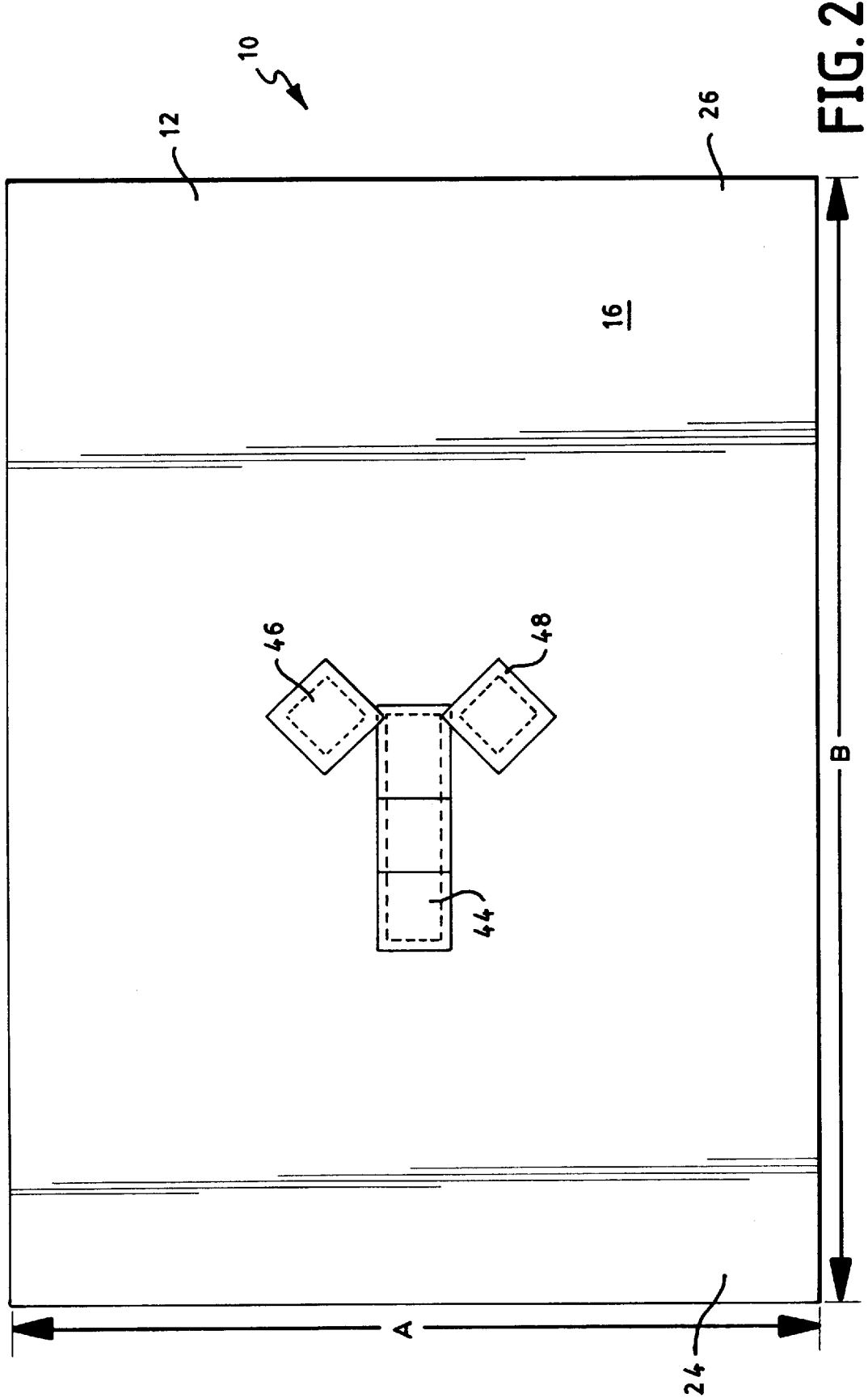
FIG. 2 is a bottom view of an embodiment of the drape, illustrating the patient-contacting surface of a drape according to the present invention.

The secondary fenestrations 20 and 22 are positioned within the base sheet 12 so that, when the drape 10 is applied to the patient, the secondary fenestrations 20 and 22 are disposed over the bone graft sites. Frequently, the bone graft sites are located on or about the iliac crests of the pelvic girdle. In such surgical procedures, either one or both of the secondary fenestrations 20 and 22 may be utilized for obtaining the bone graft required for the surgical procedure on the spine. As shown in FIGS. 1–3, the secondary fenestrations 20 and 22 are positioned near the lower portion 19 of the primary fenestration 18.

The base sheet 12 further includes a forward edge 24 and a rearward edge 26. The forward edge 24 is positioned toward the head of the patient to be covered, and the rearward edge 26 is positioned toward the feet of the patient to be covered.

Figure 4:
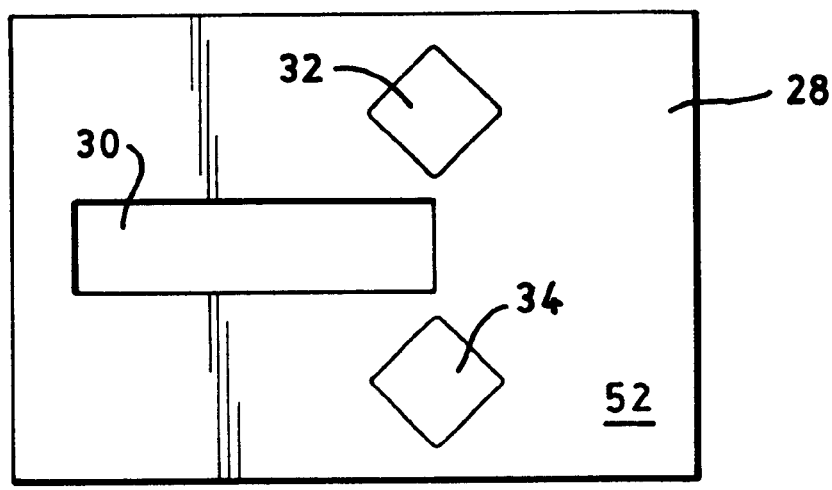
FIG. 4 is a top view of an embodiment of the reinforcement panel according to the present invention.

Referring now to FIGS. 1 and 4, a reinforcing absorbent panel 28 is shown therein. As shown in FIG. 1, the reinforcing panel 28 is superimposed on and affixed in some manner to the upper surface 14 of base sheet 12. The reinforcing panel 28 may be formed from a variety of materials, including a multi-layer laminate which includes a fluid-absorbing material that may be backed by a fluid-repellant or fluid-impervious film layer. The film-layer side or lower surface 54 of the panel 28 is secured to upper surface 14 of base sheet 12. A variety of attachment mechanisms may be used to secure the panel 28 to the upper surface 14 of the base sheet 12, such as, for example, adhesive, stitching, thermal or ultrasonic bonding. The absorbent upper surface 52 of panel 28 remains exposed and available to absorb fluids emitted from the surgical site. The fluid-impervious film layer prevents the passage of blood and other body fluids through the reinforcing panel 28 and the base sheet 12. Although many commercially available materials are suitable for use in the reinforcing panel 28, an exemplary material is available from Kimberly-Clark Corporation and is marketed under the trade name CONTROL PLUS®.

In some embodiments, the upper surface 52 of the reinforcing panel 28 may have an increased coefficient of friction to provide a slip-resistant surface to lessen the likelihood of undesired movement of surgical instruments that are placed upon the reinforcing panel 28.

The reinforcing panel 28 may be constructed of a material that has an absorbent upper surface to absorb fluids near the operative site. The reinforcing panel 28 also helps to inhibit penetration of the drape 10 by instruments that are placed on top of the reinforcing panel 28 during surgery.

Figure 9:
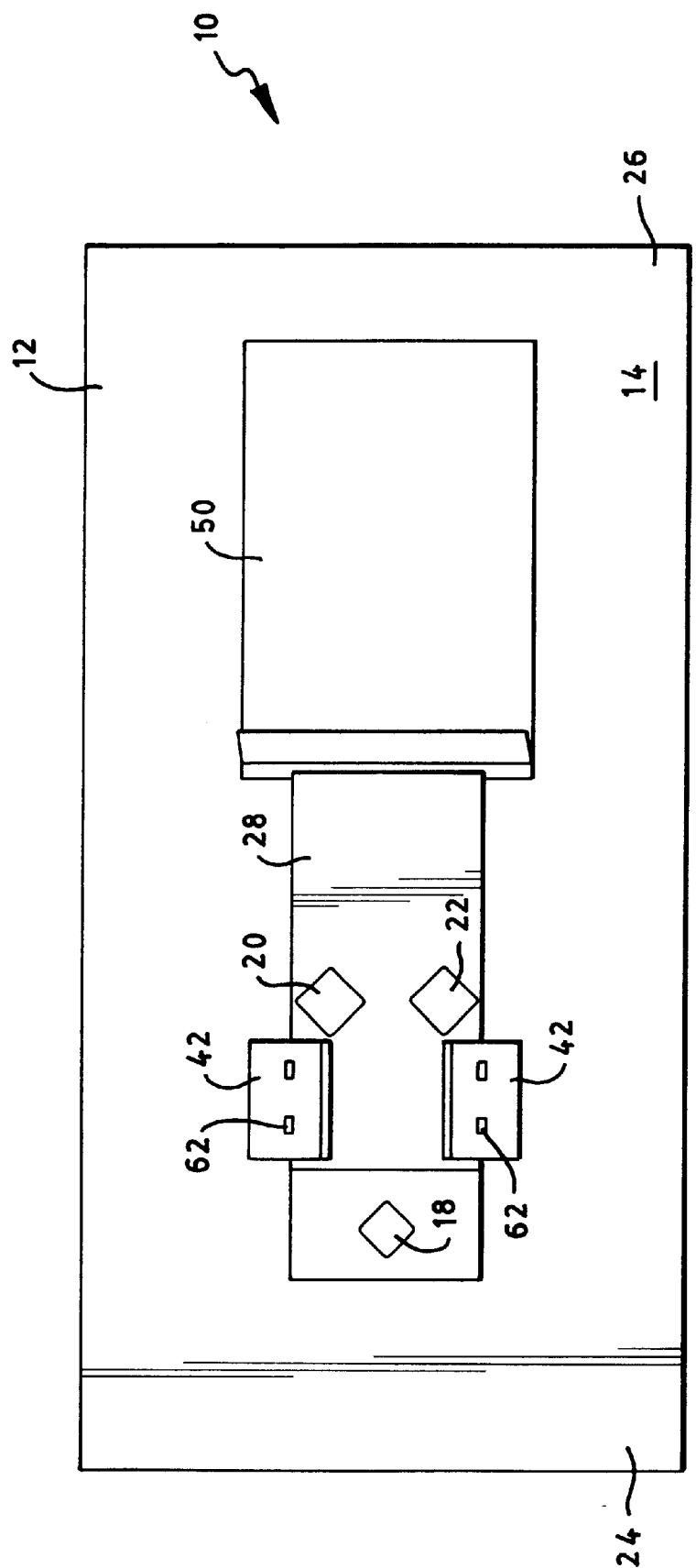
FIG. 9 is a top view of yet another embodiment of the drape according to the present invention.

As shown in FIGS. 1, 8 and 9, the reinforcing panel 28 may be disposed about the primary fenestration 18, and in some embodiments, about the secondary fenestrations 20 and 22. The reinforcing panel 28 may be positioned on the upper surface 14 of the base sheet 12 and may include reinforcement fenestrations that are aligned with the primary fenestration 18 and, if necessary, the secondary fenestrations 20 and 22. As shown in FIG. 4, fenestrations are formed in the panel 28 which, when the panel 28 is adhered to the base sheet 12, are aligned with the fenestrations formed in the base sheet 12. Specifically, the fenestration 30 formed in the reinforcing panel 28 is aligned with the primary fenestration 18 when the panel 28 is adhered to the base sheet 12. Similarly, the fenestrations 32 and 34 formed in the reinforcing panel 28 are aligned with the secondary fenestrations 20 and 22 when the panel 28 is adhered to the base sheet 12.

Figure 5:
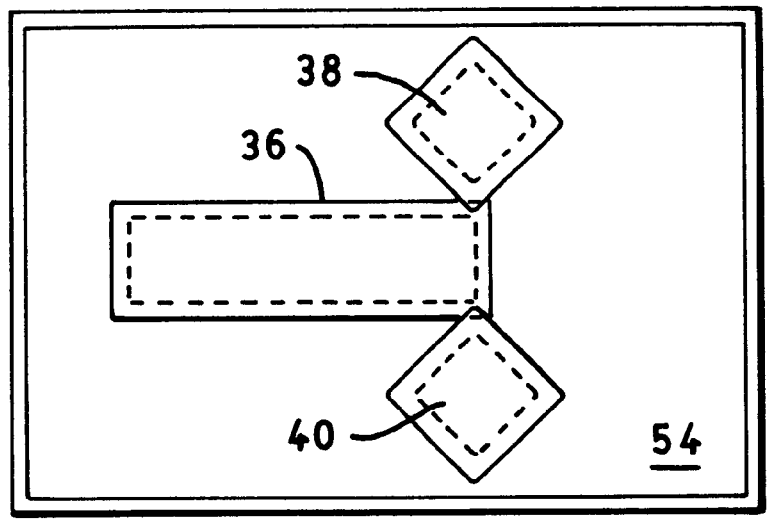
FIG. 5 is a bottom view of an embodiment of the reinforcement panel according to the present invention.
Figure 6:
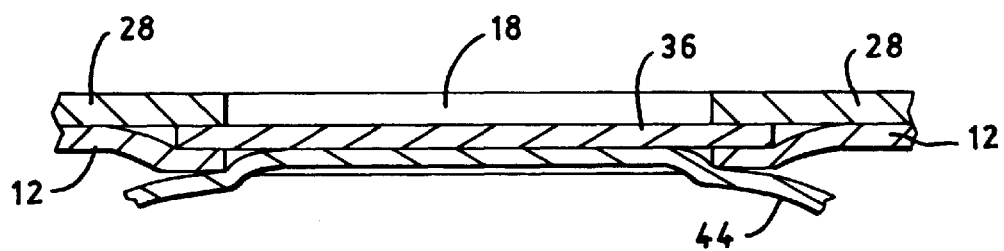
FIG. 6 is a cross-sectional view of the embodiment of the drape depicted in FIG. 1 taken along line 6—6.

Referring now to FIG. 5, an incise layer 36 may be provided and positioned over the primary fenestration 18. The incise layer 36 is, in the embodiment depicted in FIG. 1, disposed between the reinforcing panel 28 and the base sheet 12. As shown in FIG. 6, the incise layer 36 is secured to the lower surface 54 of the panel 28. If desired, an incise layer 38 may be applied over the secondary fenestration. The incise layers 36, 38 and 40 may include an adhesive side that is adapted to adhere to the patient when the drape is covering the patient. Thus, the adhesive side of the incise layer faces downwardly when the drape is positioned over the patient to provide a seal around the surgical site.

The incise layers 36, 38 and 40 may be formed from a low-density polyethylene film with adhesive on one side. For example, the incise layers may be constructed of polyethylene film available from Bertek Inc., St. Albans, Vt. 05478, or from a film available from Medical Concepts Development, Inc., St. Paul, N. Mex. 55125.

In other embodiments, strips of adhesive may be positioned around the periphery of the fenestrations 18, 20 and 22 to adhere the periphery of the fenestrations to the patient. The tacky and pressure-sensitive adhesives used may be of any biologically acceptable adhesive. Examples of such adhesive materials are described in U.S. Pat. No. 3,669,106 entitled "Surgical Drape with Adhesive Attachment Means" to Schrading et. al, which is incorporated herein in its entirety by reference.

To facilitate handling of the drape 10 and to maintain the sterility of the incise layer or, in selected embodiments, the peripheral adhesive strips, the adhesive surface may be covered with a release liner such as, for example, release liners 44, 46 and 48 shown in FIG. 2. The release liners may be formed of any of a wide variety of materials which are commonly available. For example, wax- or silicone-coated papers may be placed over the adhesive side of the incise layers until the drape 10 is applied to the patient. Alternate materials may also be utilized, such as, for example, plastic materials having at least one non-adherent surface. Such materials may be utilized when a tear-resistant release liner is appropriate. Additionally, the release layers may be segmented, as shown in FIG. 2 by release liner 44, to facilitate application of the drape 10 to the patient. In the embodiment shown in FIG. 2, the release liner 44 is segmented into three parts. Thus, the medical personnel applying the drape 10 to the patient may remove one segment of the release liner 44 at a time. This enables the medical personnel to handle a smaller exposed area of adhesive at one time, reducing the opportunities for contamination or creasing of the exposed incise layer. Additionally, the segmented release liner permits the medical personnel to determine, for each patient and/or type of surgical procedure, the length of the incise layer that must be secured to the patient. For example, a smaller patient may only need one or two of the release liners removed from the incise layer 36.

Figure 7:
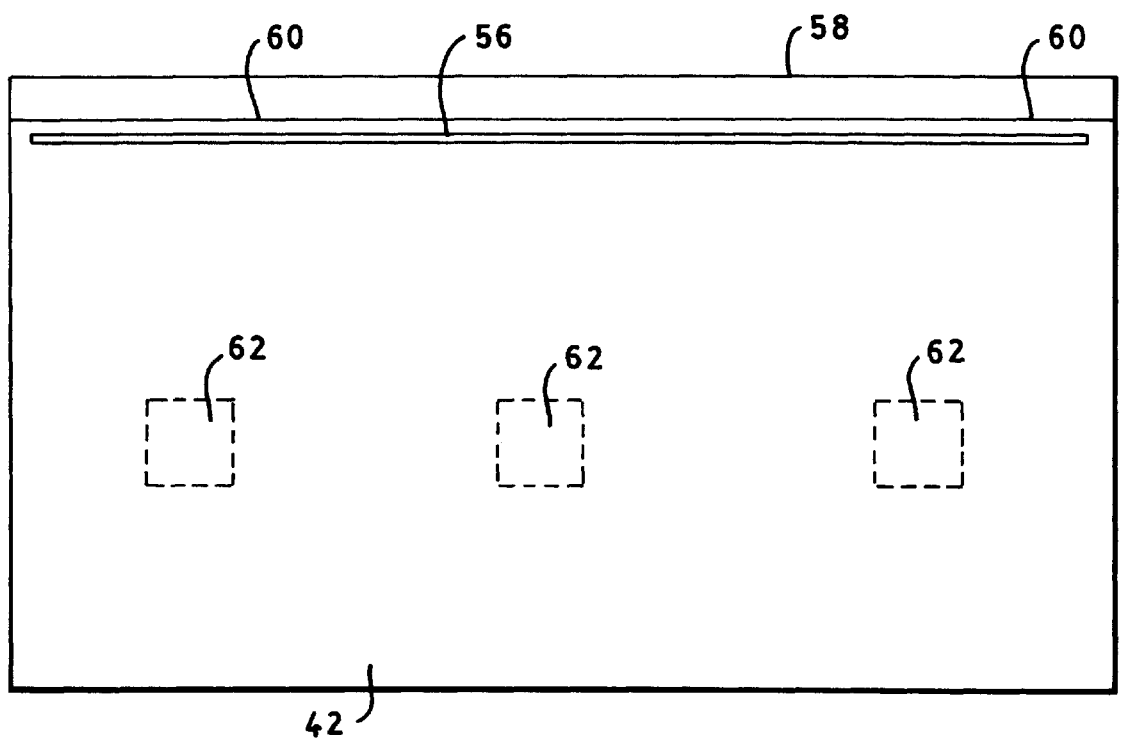
FIG. 7 is a top view of an embodiment of the pouch according to the present invention.

As shown in FIGS. 1, 7 and 8, at least one pouch 42 may be attached to the base sheet 12. The pouch 42 may be utilized to hold surgical instruments, collect fluids or a variety of other similar functions. The pouch 42 may be adhered to the base sheet 12 by adhesive such as tape and the like, stitching, or other commonly known attachment mechanisms. In some embodiments, the top edge 58 of the pouch is adhered to the upper surface 14 of the base sheet 12. The pouch 42 may include a malleable wire or strip 56 that may be positioned along the outside portion of the pouch 42 beneath the opening 60 of the pouch 42.

The lower portion of the pouch 42 may be releasably secured to the upper surface 14 of the base sheet 12 by hook-type fasteners such as fasteners 62. Such hook and loop fasteners are well known, and the use of such hook-type fasteners with nonwoven materials such as surgical drapes is common. The fasteners 62 are applied to the rear surface of the pouch 42 that will come into contact with the upper surface 14 of the base sheet 12. The use of fasteners 62 enables the pouch 42 be utilized to retain electric cords, suction lines and the like which commonly run alongside the patient. To secure such cords and lines, the lower surface of the pouch 42 is moved away from the upper surface 14 of the base sheet 12, and the cords and lines are positioned between the under side of the pouch 42 and the upper surface of the base sheet 12. The lines and cords are routed above the fasteners 62, which are then secured to the upper surface 14 of the base sheet 12. Thus, the cords and lines are retained securely between the pouch 42 and base sheet 12.

As shown in FIGS. 1 and 8, two pouches 42 may be provided, one pouch 42 being positioned on each side of the primary fenestration 18. The pouch 42 is, in some embodiments, formed of a material that is impervious to liquids, such as, for example, polyethylene or the like. The pouch 42 may be formed of a transparent or opaque material.

Figure 10:
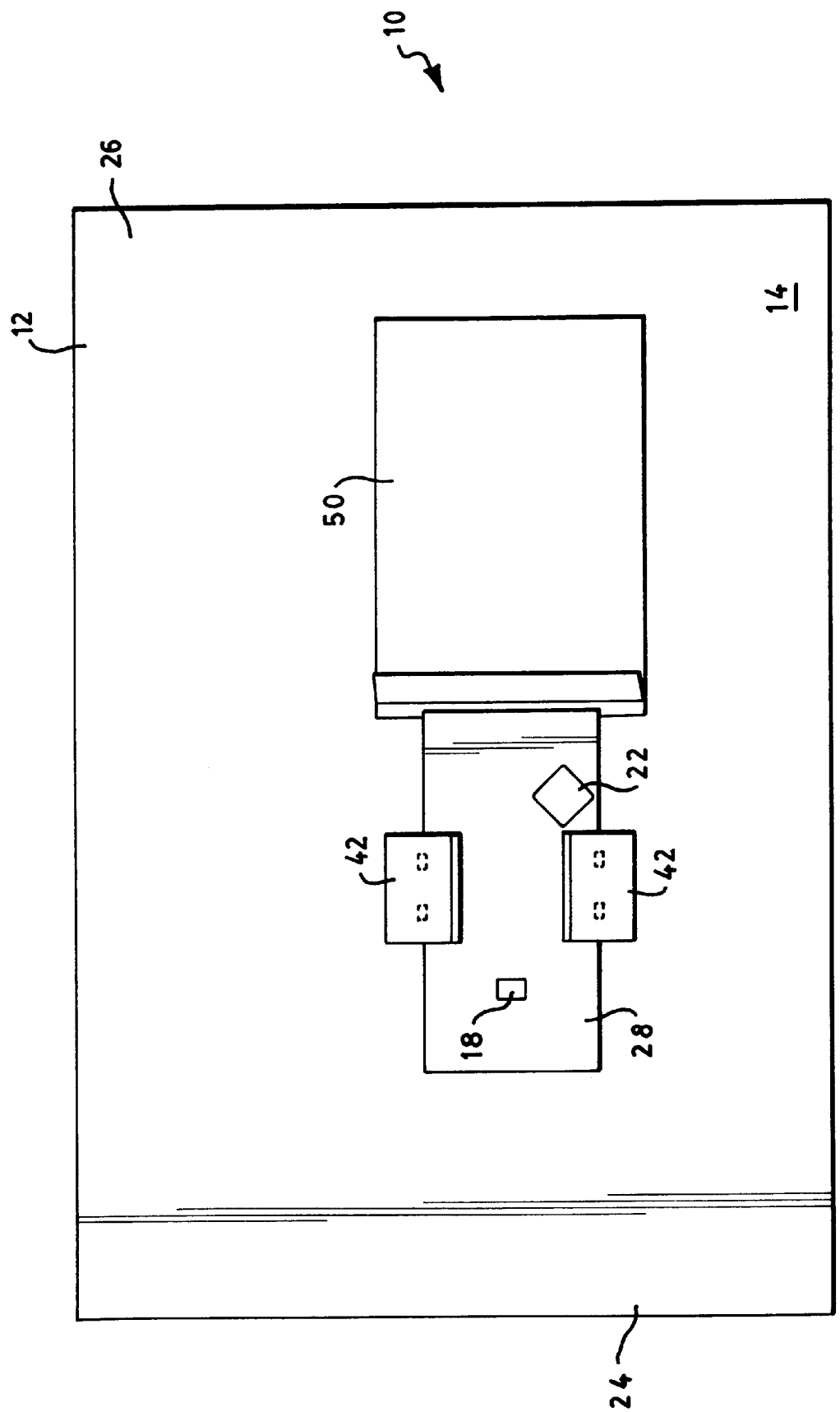
FIG. 10 is a top view of yet another embodiment of the drape according to the present invention.

The drapes depicted in FIGS. 9 and 10 are useful in spinal surgeries which use the anterior approach, that is, the surgery is performed with the patient lying on their back. As shown in FIG. 9, the primary fenestration 18 is square and spaced apart from the secondary fenestrations 20 and 22. As shown in FIG. 10, the primary fenestration is rectangular and spaced apart from a single secondary fenestration 22. In such an embodiment, the single secondary fenestration may encompass the area of the patient that may be covered by two separate fenestrations. For example, a single rectangular fenestration may be utilized that extends across the patient to encompass both bone graft sites.

In the drapes shown in FIGS. 9 and 10, two pouches 42 are attached to the reinforcement panel 28. The fasteners 62 are shown therein in dotted lines. The drape 10 may further include a table cover, such as an overhead table cover 50 shown in FIGS. 9 and 10. The table cover may be variously attached to the drape to enable a table that is suspended over the patient during surgery to be covered by a single drape.

Figure 11:
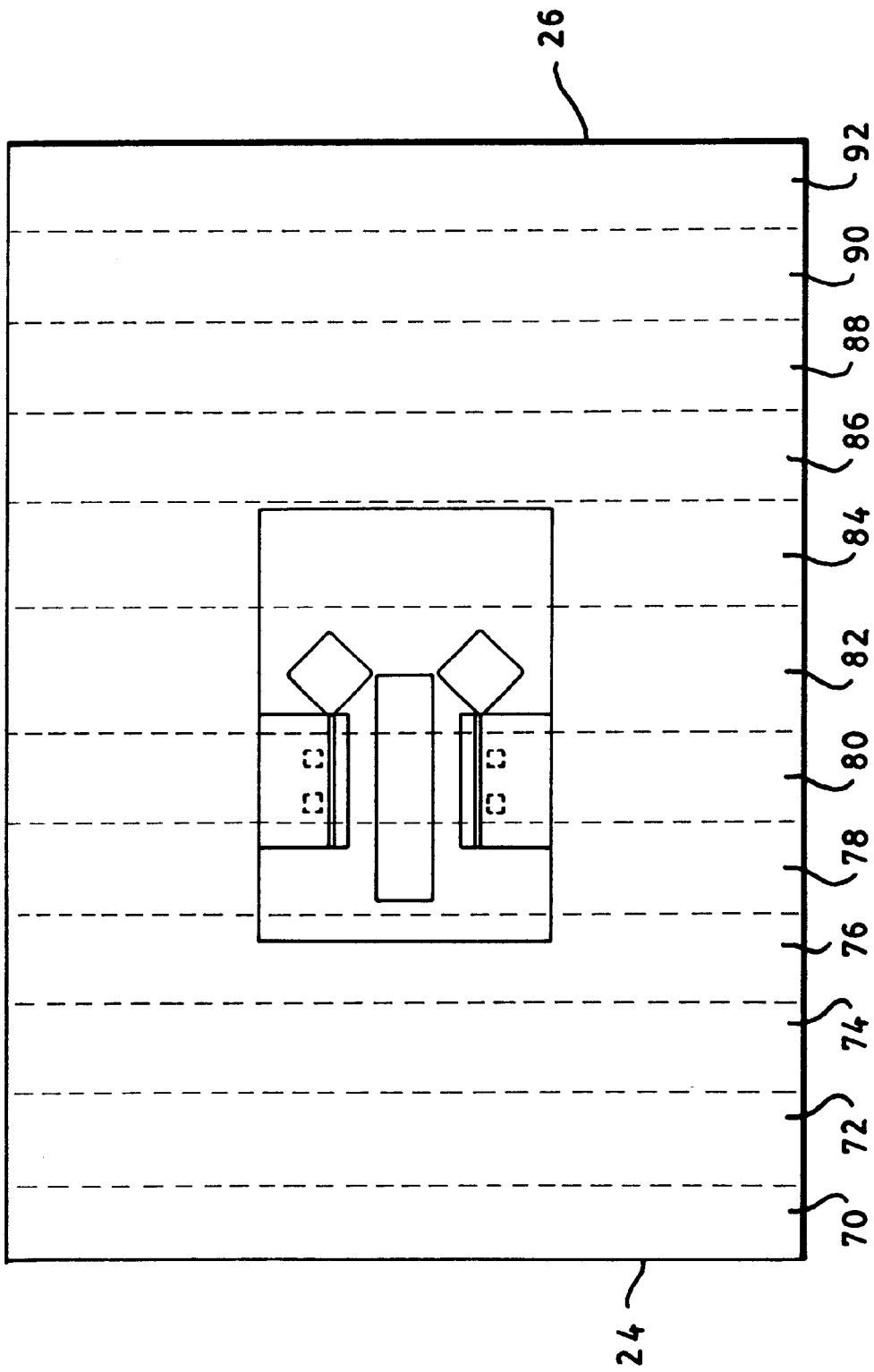
FIG. 11 is a top view of a drape according to the present invention illustrating lines along which the drape may be folded.
Figure 12:
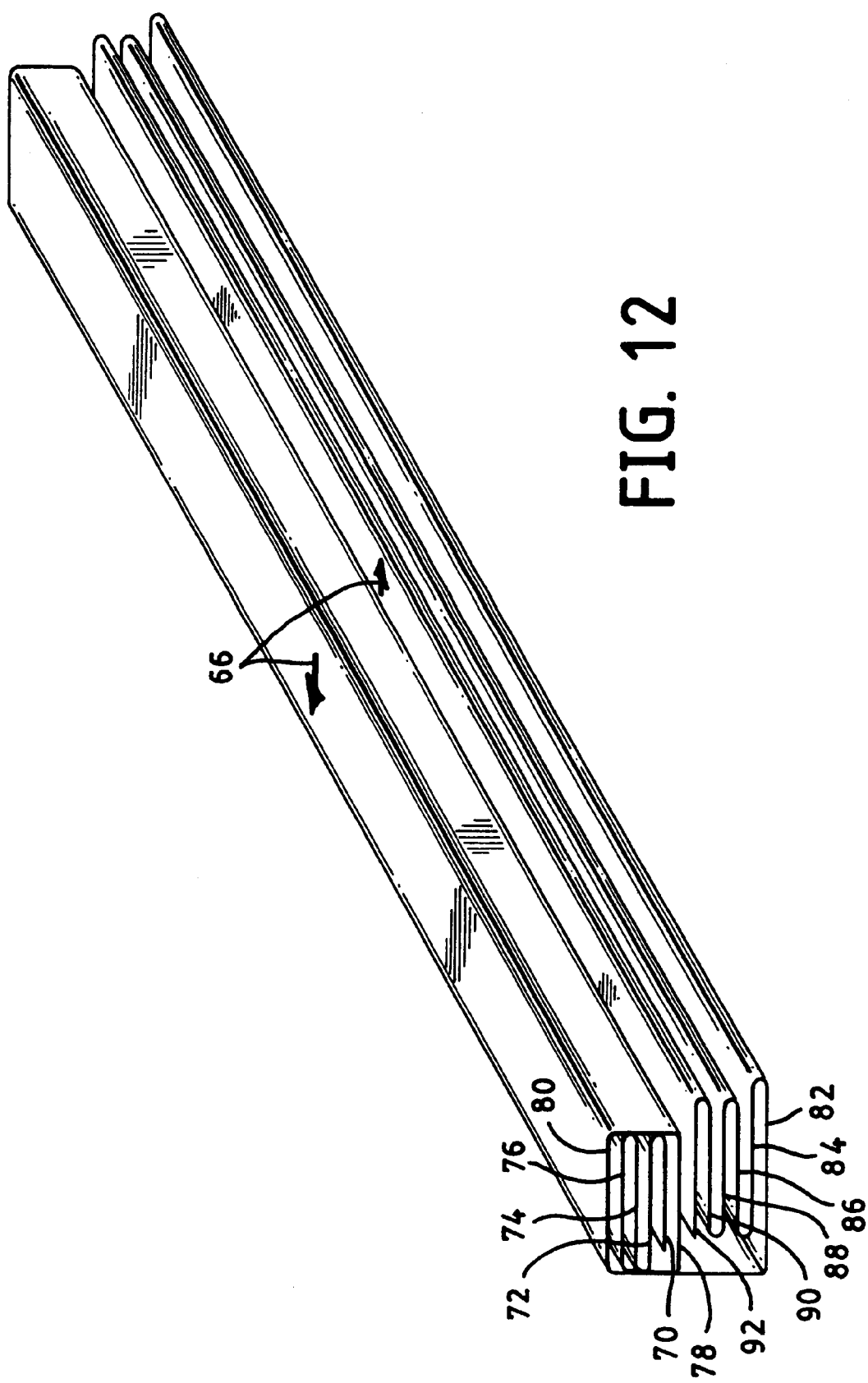
FIG. 12 is a perspective view of an embodiment of the drape of the present invention that is partially folded.

As shown in FIGS. 11–17, the drape 10 may be folded in a variety of manners to assist the medical personnel in applying the drape 10 to the patient. Referring to FIG. 11, the drape 10 is shown therein with the upper surface 14 of the base sheet 12 facing up. The length B of the drape 10 is divided into segments 70, 72, 74, 76, 78, 80, 82, 84, 86, 88, 90 and 92, as indicated by the dotted lines in FIG. 11. Each segment is rectangular in shape, with the longer dimension of each segment extending along the width A of the drape. Segment 70 is disposed at the forward edge 24 of the base sheet 12. Segment 92 is disposed at the rearward edge 26 of the base sheet 12. The segments 72–90 extend therebetween. The segments may have differing widths to enable medical personnel to more easily grasp selected segments for unfolding and applying the drape to a patient.

A perspective view of the drape 10 after being folded along the dotted lines indicated in FIG. 11 clearly shows the folding scheme. Widths of the folds are exaggerated in FIG. 12 to enable the folding scheme to be clearly seen. Starting at the forward edge 24, the segment 70 is folded toward the central portion of the drape 10 so that the segment 70 overlies the segment 72. Next, the segments 70 and 72 are folded toward the central portion of the drape 10 and underneath the segment 74 so that the segment 72 is adjacent to the segment 74. Next, the segments 70, 72 and 74 are grasped and folded toward the central portion of the drape 10 so that the segment 74 is adjacent to the segment 76. The folded segments 70, 72, 74 and 76 are then folded toward the central portion of the drape 10 so that the segment 70 is adjacent to the segment 78.

Next, the segment 92, which is the segment that borders the rearward edge 26 of the base sheet 12, is folded toward the central portion of the drape 10 so that the segment 92 overlies the segment 90. The segments 90, 88, 86, 84 and 82 are then fan-folded toward the central portion of the drape 10 so that the segment 90 is disposed between the segments 92 and 88, and the segment 86 is disposed between the segments 88 and 84, and the segment 84 is disposed between the segments 86 and 82. Next, the drape is folded so that segment 78 is adjacent to segment 92.

Figure 13:
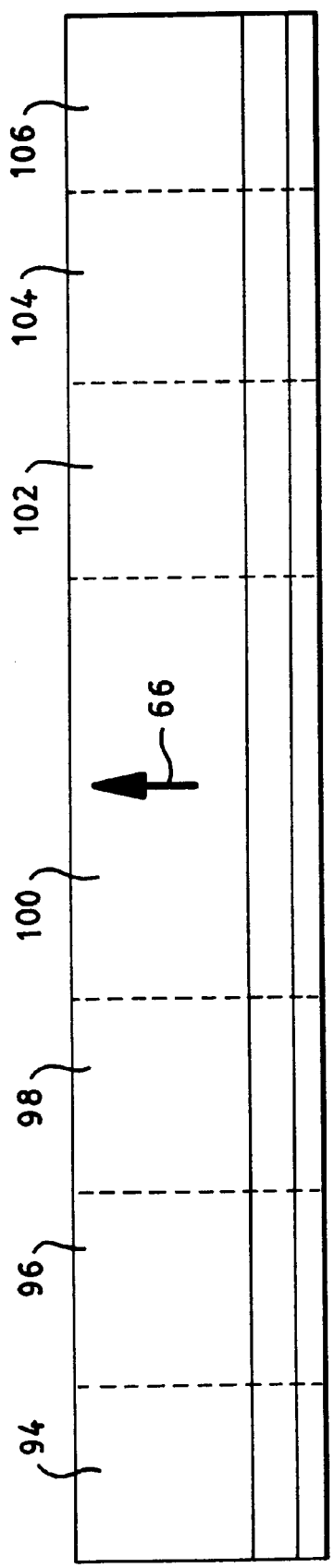
FIG. 13 is a top view of an embodiment of the drape of the present invention that is partially folded.
Figure 14:
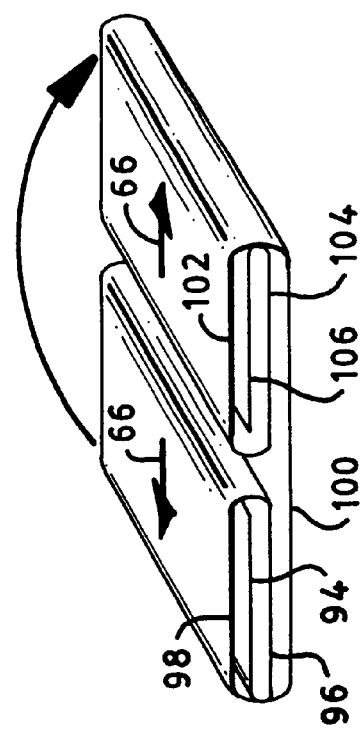
FIG. 14 is a perspective view of an embodiment of the drape of the present invention that is partially folded.

FIG. 13 is a top view of the drape 10 after it has been folded along the length dimension B. The drape 10 is divided into segments 94, 96, 98, 100, 102, 104 and 106 along its width or A dimension. The segment 94 is at the leftmost portion of the drape 10 shown in FIG. 13, and the segment 106 is the rightmost portion of the drape 10. The segments 96–104 extend therebetween. As illustrated in FIG. 14 and starting at the rightmost portion of the drape, the segment 106 is folded so that it overlies the segment 104. Next, the segments 106 and 104 are folded so that segment 106 is disposed between the segments 102 and 104. The segments 106, 104, and 102 are then folded toward the central portion of the drape 10 so that the segment 104 overlies the segment 100. Turning to the leftmost portion of the drape 10, the segment 94 is folded toward the central portion of the drape 10 so that the segment 94 overlies the segment 96. The segments 94 and 96 are then folded so that the segment 94 is disposed between the segments 98 and 96. The segments 94, 96, and 98 are then folded toward the central portion of the drape 10 so that the segment 96 is disposed between the segments 100 and 94.

Figure 15:
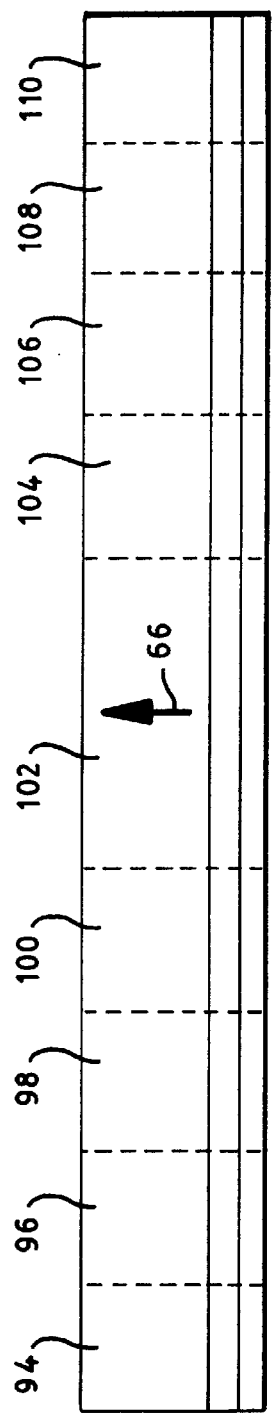
FIG. 15 is a top view of an embodiment of the drape of the present invention that is partially folded.
Figure 17:
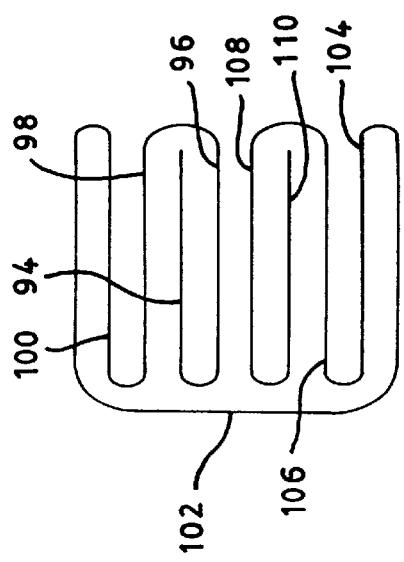
FIG. 17 is a side view of an embodiment of the drape of the present invention that is folded.
Figure 16:
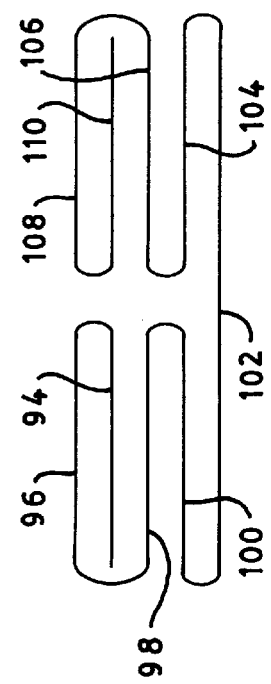
FIG. 16 is a side view of an embodiment of the drape of the present invention that is partially folded.

An alternate folding scheme is shown in FIGS. 15–17. FIG. 15 is a top view of the drape 10 after it has been folded along the length dimension B. The drape 10 is divided into segments 94, 96, 98, 100, 102, 104, 106, 108, and 110 along its width or A dimension. The segment 94 is at the leftmost portion of the drape 10 shown in FIG. 13, and the segment 106 is the rightmost portion of the drape 10. The segments 96-110 extend therebetween.

Looking at the rightmost portion of the drape 10 as depicted in FIG. 15, the segment 110 is folded toward the central portion of the drape 10 so that the segment 110 is adjacent to the segment 108. The segments 110 and 108 are then folded so that the segment 110 is disposed between the segments 108 and 106. The segments 110, 108 and 106 are then folded toward the central portion of the drape 10 so that the segment 106 is adjacent to the segment 104. The segments 110, 108, 106 and 104 are then folded so that the segment 104 is adjacent to the segment 102.

Looking now toward the leftmost portion of the drape 10 as shown in FIG. 15, segment 94 is folded toward the central portion of the drape so that the segment 94 is adjacent to the segment 96. The segments 94 and 96 are then folded so that the segment 94 is disposed between the segments 96 and 98. The segments 94, 96, and 98 are then folded toward the central portion of the drape 10 so that the segment 98 is adjacent to the segment 100. The segments 94, 96, 98 and 100 are then folded so that the segment 100 is adjacent to the segment 102. This folding scheme is depicted in FIG. 16. Once the drape 10 has been folded thusly, the drape may be folded again so that the segment 96 is adjacent to the segment 108, as shown in FIG. 17.

Figure 18:
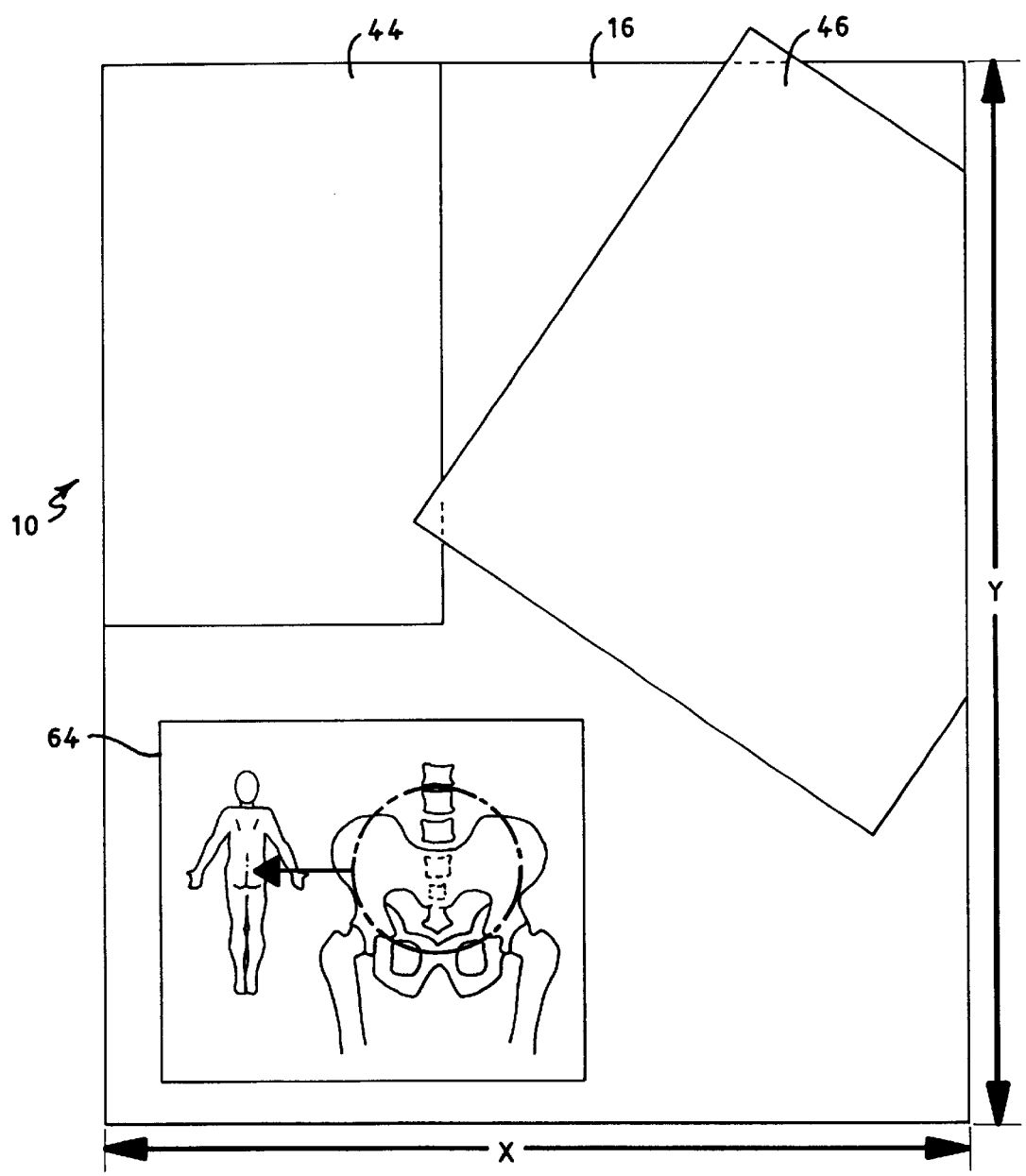
FIG. 18 is a top view of an embodiment of the drape of the present invention that is folded.

FIG. 18 is a top view of a fully folded drape 10 that is ready to be applied to a patient. The surgical drape 10 of the present invention may be folded so that, as medical personnel apply the drape to the patient, the lower surface 16 of the drape 10 is on the exterior of the folded drape as shown in FIG. 18. As shown therein, the release layer 44 covering the primary fenestration 18 is clearly visible and easily accessible by medical personnel. In embodiments where the release layer 44 that is disposed over the incise layer 36 of the primary fenestration 18 is segmented, the medical personnel applying the drape 10 to the patient may expose only a portion of the adhesive side of the incise layer 36. This facilitates application of the drape 10 to the patient while minimizing the opportunities for contamination of the incise layer.

Directions may be stamped, printed or adhered to the drape to indicate how the drape is to be placed on the patient. For example, arrows such as arrows 66 in FIGS. 13 and 14, as well as other diagrams, such as the diagram shown in FIG. 18 at 70, may be utilized and applied to any portion of the surgical drape in any of a wide variety of manners.

As used herein and in the claims, the term "comprising" is inclusive or open-ended and does not exclude additional unrecited elements, compositional components, or method steps.

While the invention has been described in detail with respect to specific preferred embodiments thereof, it will be appreciated that those skilled in the art, upon attaining an understanding of the foregoing, may readily conceive of alterations to and variations of the preferred embodiments. Such alterations and variations are believed to fall within the scope and spirit of the invention and the appended claims.

I claim:

1. A surgical drape for covering a patient during a surgical procedure, the drape comprising:

a base sheet having an upper surface, a lower surface, a forward edge, and a rearward edge;

a primary fenestration formed in the base sheet positionable over the patient so that the primary fenestration is disposed proximate to the spine of the patient through which a surgical procedure may be performed when the drape is covering a patient;

at least one secondary fenestration formed in the base sheet through which a second surgical procedure may be performed when the drape is covering a patient;

an incise layer extending across the primary and secondary fenestrations, the incise layer having an adhesive side that is adapted to adhere to the patient when the drape is covering the patient; and a reinforcement panel disposed about the primary fenestration, the reinforcement panel being positioned on the upper surface of the base sheet and having a reinforcement fenestration that is aligned with the primary fenestration.

2. The drape of claim 1, the drape adapted to be positionable over the patient so that the secondary fenestration is disposed proximate to the bone graft site of the patient.

3. The drape of claim 1, further including at least one pouch attached to the upper surface of the drape.

4. The drape of claim 3, the pouch adapted to hold surgical instruments.

5. The drape of claim 3, the pouch including an upper portion which is attached to the upper surface of the drape, and further including a lower portion which is releasably attachable to the upper surface of the drape.

6. The drape of claim 5, the lower portion of the pouch including at least one hook-type fastener.

7. The drape of claim 1 having two secondary fenestrations.

8. The drape of claim 7, the primary fenestration having a lower portion disposed nearest the rearward edge of the base sheet, the secondary fenestrations being positioned proximate to the lower portion of the primary fenestration.

9. The surgical drape of claim 1, the drape being folded so that the primary fenestration is visible.

10. The surgical drape of claim 9, the drape being folded so that the lower side of the drape is visible.

11. The surgical drape of claim 1, the reinforcement panel disposed about the primary and secondary fenestrations.

12. The drape of claim 1, wherein the incise layer comprises a plurality of separate incise layers.

13. A surgical drape for covering a patient during a surgical procedure, the drape comprising:

a base sheet having an upper surface, a lower surface, a forward edge, and a rearward edge;

a primary fenestration formed in the base sheet positionable over the patient so that the primary fenestration is disposed proximate to the spine of the patient through which a surgical procedure may be performed when the drape is covering a patient;

at least one secondary fenestration formed in the base sheet through which a second surgical procedure may be performed when the drape is covering a patient;

a reinforcement panel disposed about the primary fenestration, the reinforcement panel being positioned on the upper surface of the base sheet and having a reinforcement fenestration that is aligned with the primary fenestration; and a diagram illustrating how to apply the drape to the patient for spinal surgery.

14. The drape of claim 13, further including an incise layer extending across the primary and secondary fenestrations, the incise layer having an adhesive side that is adapted to adhere to the patient when the drape is covering the patient.

15. The drape of claim 13, the drape adapted to be positionable over the patient so that the secondary fenestration is disposed proximate to the bone graft site of the patient.

16. The drape of claim 13, further including at least one pouch attached to the upper surface of the drape.

17. The drape of claim 16, wherein the pouch includes an upper portion which is attached to the upper surface of the drape, and further includes a lower portion which is releasably attachable to the upper surface of the drape.

18. The drape of claim 13 having two secondary fenestrations.

19. The drape of claim 18, the primary fenestration having a lower portion disposed nearest the rearward edge of the base sheet, the secondary fenestrations being positioned proximate to the lower portion of the primary fenestration.

20. The drape of claim 13, the reinforcement panel disposed about the primary and secondary fenestrations.

* * * * *